United States Patent [19]
Cibis et al.

[11] Patent Number: 5,502,520
[45] Date of Patent: Mar. 26, 1996

[54] METHOD AND APPARATUS FOR DETECTING EYE DISORDERS

[76] Inventors: Gerhard W. Cibis, 1268 W. 57th St., Kansas City, Mo. 64113; Thomas P. Luke, 3721 SW. Harbor Cir., Lee's Summit, Mo. 64082

[21] Appl. No.: 162,865

[22] Filed: Dec. 3, 1993

[51] Int. Cl.$^6$ .................... A61B 3/14; A61B 3/00
[52] U.S. Cl. .................... 351/206; 351/200; 351/246
[58] Field of Search ........................ 351/200, 201, 351/202, 205, 206, 221, 246; 354/62

[56] References Cited

U.S. PATENT DOCUMENTS

| | | | |
|---|---|---|---|
| 3,544,203 | 12/1968 | Garcia | 351/201 |
| 3,574,464 | 4/1971 | Howland | 356/126 |
| 3,587,335 | 6/1971 | Howland | 74/89.15 |
| 3,619,067 | 11/1971 | Howland | 356/125 |
| 3,879,113 | 4/1975 | Howland et al. | 351/206 |
| 3,940,608 | 2/1976 | Kissinger et al. | 250/227.28 |
| 3,947,186 | 3/1976 | Howland | 351/241 |
| 4,140,369 | 2/1979 | Howland | 359/452 |
| 4,257,690 | 3/1981 | Howland | 351/239 |
| 4,274,737 | 6/1981 | Howland | 356/124.5 |
| 4,523,820 | 6/1985 | Kaakinen | 351/206 |
| 4,586,796 | 5/1986 | Molteno | 351/206 |
| 4,669,836 | 6/1987 | Richardson et al. | 351/206 |
| 4,717,952 | 1/1988 | Kohayakawa et al. | 358/113 |
| 4,989,968 | 2/1991 | Freedman | 351/206 |

FOREIGN PATENT DOCUMENTS 2690329  10/1993  France ................... 351/206

OTHER PUBLICATIONS

Russell D. Hamer, Ph.D. et al., "Comparison of On– and Off–Axis Photorefraction With Cycloplegic Retinoscopy in Infants", *Journal Pediat. Ophthalmol. Strabismus*, vol. 29, pp. 232–239 (Jul./Aug. 1992).

Gian Paolo Paliaga, M.D., "Major Review: Linear Strabismometric Methods", *Binocular Vision Quarterly*, vol. 7 (No. 3), pp. 139–154 (Summer 1992).

R. M. Ingram, "Refraction of 1–year–old Children After Atropine Cycloplegia", *British Journal of Ophthalmology*, vol. 63, pp. 343–347 (1979).

R. M. Ingram et al., "Screening For Refractive Errors at Age 1 Year : A Pilot Study", pp. 243–250. No Date.

Matthew L. Ehrlich, M.D. et al., "Preschool Vision Screening for Amblyopia and Strabismus. Programs, Methods, Guidelines, 1983", *Survey of Ophthalmology*, vol. 28 (No. 3), pp. 145–163 (Nov. 12, 1983).

Howard C. Howland, "Optics of Photoretinoscopy: Results from Ray Tracing", *American Journal of Optometry & Physiological Optics* vol. 62, (No. 9) pp. 621–625 (Sep. 1985).

W. R. Bobier et al. "Eccentric Photorefraction: Optional Analysis and Empirical Measures", *American Journal of Optometry & Physiological Optics*, vol. 62, No. 9, pp. 614–620 (Sep. 1985).

Creig S. Hoyt, "Photorefraction—A Technique for Preschool Visual Screening", *Arch. Ophthalmol.*, vol. 105, pp. 1497–1498 (Nov. 1987).

Keith S. Morgan, M.D. et al., "Clinical Evaluation of a Commercial Photorefractor", *Arch. Ophthalmol*, vol. 105, pp. 1528–1533 (Nov. 1987).

(List continued on next page.)

*Primary Examiner*—William L. Sikes
*Assistant Examiner*—Huy Mai
*Attorney, Agent, or Firm*—Shook, Hardy & Bacon

[57] ABSTRACT

A medical device and method are provided for performing and recording Brueckner and Hirschberg reflex tests without the assistance of an eye specialist. The device comprises a video apparatus for taking and recording real time video of the eyes of a patient and a light source for producing a beam of light at a lens of the video apparatus. The beam of light is directed into the eyes of the patient and the eye reflex response is recorded on the video. A video segment which includes the focusing of the patient's eyes on a desired object is then forwarded to the eye specialist for diagnosis of eye disorders indicated by the Brueckner and Hirschberg reflex tests.

12 Claims, 2 Drawing Sheets

OTHER PUBLICATIONS

D. E. Shaw, "Amblyopia—Factors Influencing Age of Presentation", *The Lancet*, vol. II, No. 8604, pp. 207–209 (Jul. 23, 1988).

Paul E. Romano, "Advances in Vision and Eye Screening: Screening at Six Months of Age", *Pediatrician*, vol. 17, pp. 134–139 (1990).

Patrick A. DeRespinis, M.D. et al., "Calibration of Hirschberg Test Photographs under Clinical Conditions", *Ophthalmology*, vol. 96, No. 7, pp. 946–949 (Jul. 1989).

Paul E. Romano, M.D., "New Technology Applicable to Eye and Vision Screening", *Vision and Eye Screening*, pp. 140–141 (Sep. 1989).

Larry D. Roe, M.D., "The Light That Leaks: Brückner and the Red Reflex", *Survey of Ophthalmology*, vol. 28, No. 6, pp. 665–670 (May/Jun. 1984).

I. J. Hodgkison et al., "Characterization of the Fundal Reflectance of Infants", *Optometry and Vision Science*, vol. 68, No. 7, (1991) pp. 513–521.

Wolfgang Wesemann et al., "Theory of Eccentric Photorefraction (Photoretinoscopy): Astigmatic Eyes", *J. Opt. Soc. Am.A*, vol. 8 No. 12, pp. 2038–2047, (Dec. 1991).

Ian J. Hodgkinson et al., "Photorefraction of the Living Eye: A Model for Linear Knife Edge Photoscreening", *Applied Optics*, vol. 30, No. 16, pp. 2263–2269 (Jun. 1991).

R. M. Ingram et al., "Refraction as a Means of Predicting Squint or Amblyopia in Preschool Siblings of Children Known to Have These Defects", *British Journal of Ophthalmology*, vol. 63, pp. 238–242 (1979).

E. Neumann, M.D., "Prevention of Strabismic Amblyopia of Early Onset With Special Reference to the Optimal Age for Screening".

*Journal of Pediatric Ophthalmology & Strabismus*, vol. 24, No. 3, pp. 106–110 (May/Jun. 1987).

Susan H. Day, M.D., et al., "Photographic Detection of Amblyogenic Factors", *Ophthalmology*, vol. 93, No. 1, (Jan. 1986).

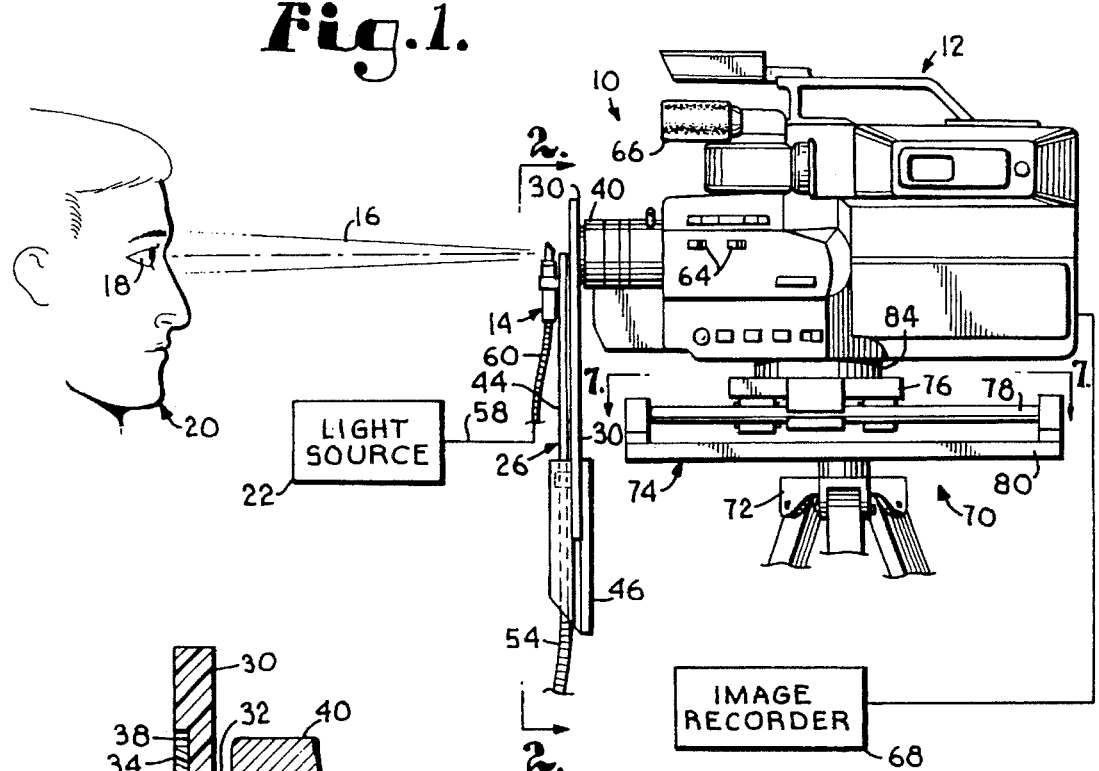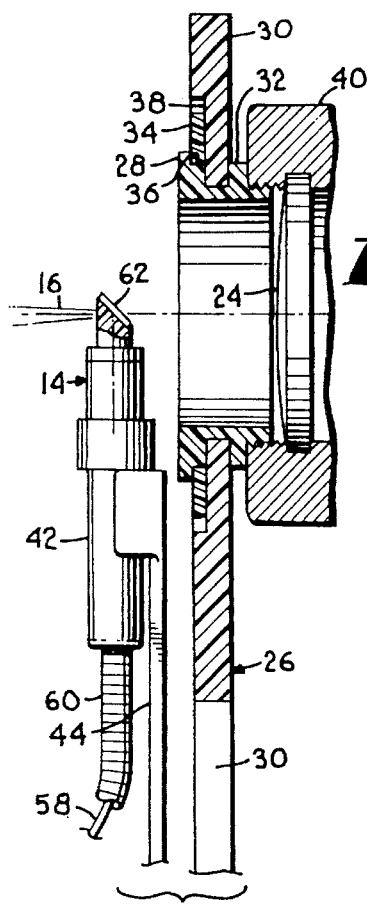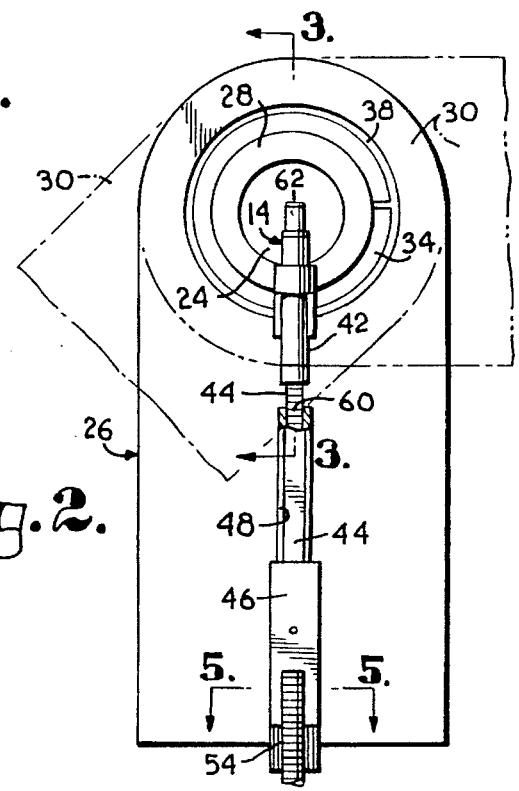

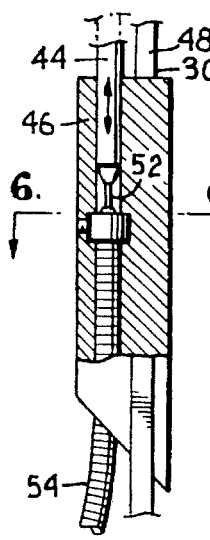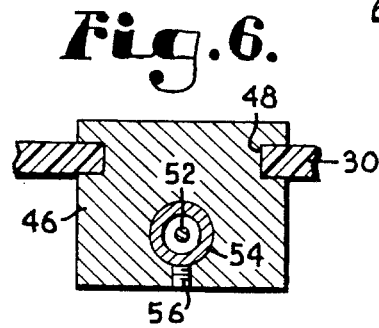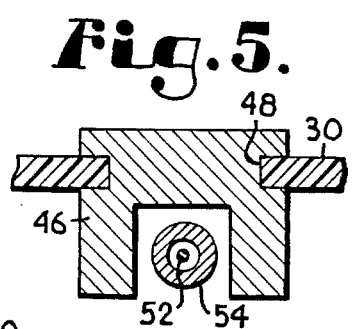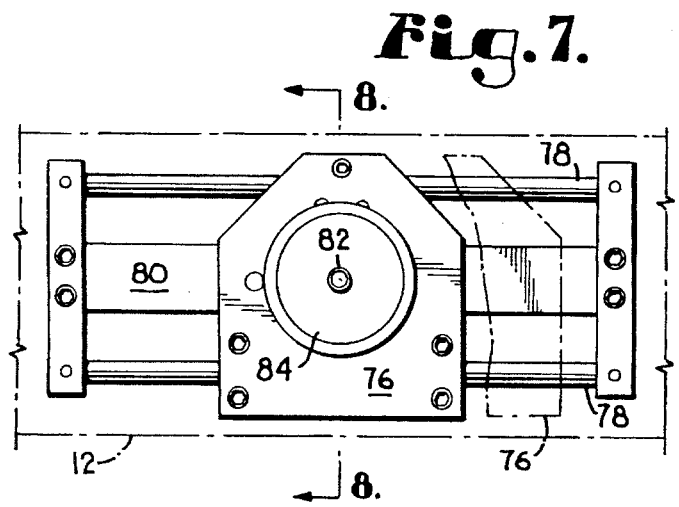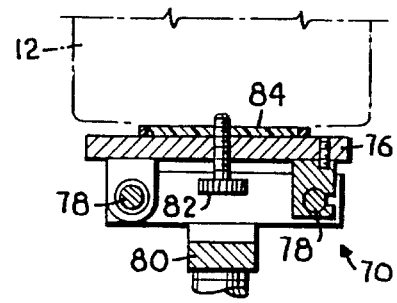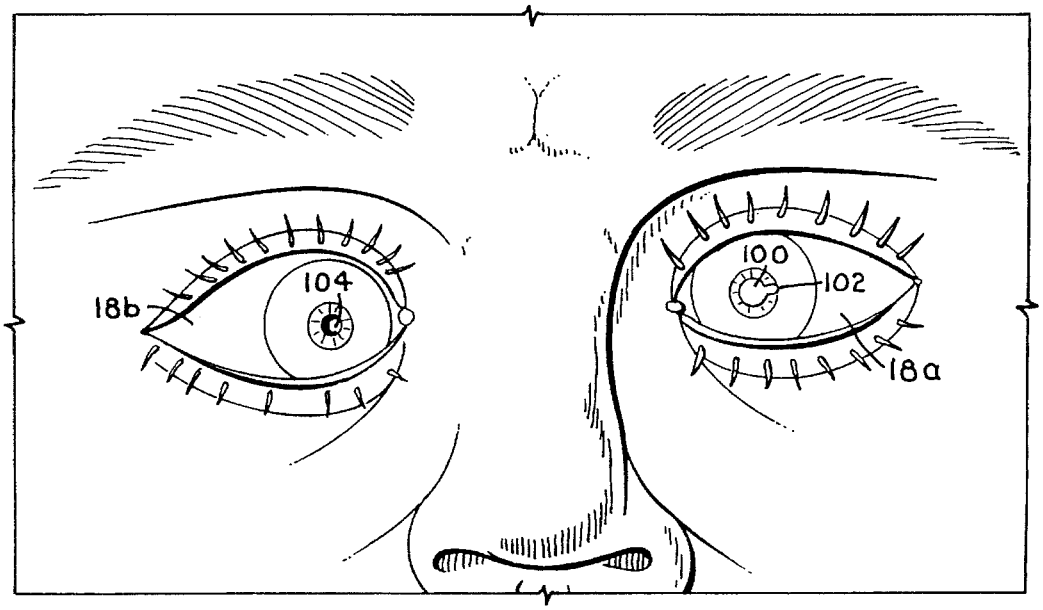

METHOD AND APPARATUS FOR DETECTING EYE DISORDERS

BACKGROUND OF THE INVENTION

This invention relates in general to eye disorders and, more particularly, to a method and apparatus for using a reflected light to detect eye disorders.

Many types of eye disorders can be diagnosed by reflecting light off of portions of an individual's eyes and observing the pattern of the reflected light. One of these diagnostic tests is known as the Brueckner test and utilizes an ophthalmoscope to compare the red reflexes of both eyes. When both eyes simultaneously fixate and focus on the ophthalmoscope light source, both pupils constrict, the corneal light reflexes become centered and both red reflexes become quite dark. A difference in the brightness of the two reflexes indicates binocular asymmetry, which may mean that the individual has either strabismus or anisometropia.

To accurately diagnose eye problems using the Brueckner test, an eye specialist must focus the light source upon the eyes of the patient for a period of time to allow the eyes of the patient to fixate and focus. However, this type of examination of young children and other noncompliant individuals can be extremely difficult because of the need for the individual to remain still and focused on the light source or other desired object. The difficulty in examining young children is particularly problematic because early detection of certain types of visual defects is important in order to allow corrective measures to be undertaken before permanent or more serious disorders result.

Eye specialists are trained to recognize when the patient's eyes are properly fixated and focused on the light source during eye examinations, and at that point the eye specialist can diagnose any problems that may be visualized by the reaction of the eyes to the light. General medical practitioners, however, typically lack sufficient training to diagnose eye problems using Brueckner and Hirschberg reflex tests which implement a light source to stimulate the eye. The inability of many general practitioners to diagnose eye disorders greatly reduces the opportunity to fully screen patients during general medical checkups. Accordingly, it would be desirable to allow a patient to visit one doctor to obtain a complete checkup, instead of making separate visits to an eye specialist for diagnosis of potential eye problems.

Prior attempts have been made at using photographic equipment to capture an eye testing session on still photographs. However, such a prior art method of diagnosing special eye problems has proved ineffective in many instances because the photographs must be taken when a patient's eyes have constricted so that an accurate Brueckner and Hirschberg analysis can be performed. The camera operator, even with extensive training, may fail to capture the essential time segment when the eyes of the patient are properly constricted, particularly when the patient is a young child or noncompliant individual. The resulting photograph may thus fail to yield the necessary visual data to perform Brueckner and Hirschberg reflex tests and may cause misdiagnoses because the eye specialist is unable to determine from the photograph whether the patient's eyes were properly focused on the camera or other intended object.

SUMMARY OF THE INVENTION

It is an object of this invention to provide a medical device which can be used in a process for diagnosing certain eye disorders and requires only momentary fixation of the patient's eyes so that diagnosis of young children or other individuals can be readily performed.

It is another object of this invention to provide a medical device which can be used in a process for diagnosing certain eye disorders but does not require the immediate assistance of an eye specialist to produce the eye response necessary for diagnosing such disorders.

As a corollary to the preceding object, it is a further object of this invention to provide a medical device which can be used for conducting Brueckner and Hirschberg reflex tests and recording the visual response so that general screening of individuals can be performed by trained personnel and the results can be reviewed and diagnosed by an eye specialist at a later time.

It is also an object of this invention to provide a diagnostic procedure which allows Brueckner and Hirschberg reflex tests to be conducted by nurses or other trained personnel with the results recorded on video film so that an eye specialist can review the video and determine the precise moment at which the patient's eyes have focused on the light source so that more accurate diagnosis of certain eye disorders can be conducted without the need for the eye specialist to be present during the actual testing.

It is yet another object of this invention to provide a medical device which allows non-specialist physicians and staff members to record real time video images of the eyes of a patient so that the images can be forwarded to a specialist to determine if the patient requires further special eye care, thereby greatly increasing the opportunity to detect eye disorders as a result of routine general medical screenings.

It is a further object of this invention to provide an eye medical device which allows a patient to obtain comprehensive eye testing from a general practitioner without the need for, and the costs associated with, a separate visit to an eye specialist.

It is a yet further object of this invention to provide an eye medical device which can utilize existing video cameras so that the device is relatively inexpensive and can be readily afforded by general practitioners.

To accomplish these and other related objects of the invention, a medical device is provided for recording real time images of a light beam reflected off of the eyes of a patient, said device comprising:

a video image recorder for recording real time video of the eyes of the patient and including a lens for focusing a video image onto a recording medium;

a light emitting device coupled with the video image recorder for directing a beam of light into the eyes of the patient; and means for mounting the light device on the video image recorder to allow the beam of light to be directed from variable positions within a field of the lens so that light reflected from the patient's eyes and recorded onto the recording medium travels along a path generally coincident with that of the beam of light.

In another aspect, the invention comprises a method for performing Hirschberg and Brueckner reflex tests on the eyes of an individual without the immediate assistance of an eye specialist, the method comprising the steps of:

directing a beam of light from within a field of a lens of a video camera onto the eye of the individual to produce Hirschberg and Brueckner reflexes;

focusing the eyes of the patient on an object while the Hirschberg and Brueckner reflexes are produced;

recording the Hirschberg and Brueckner reflexes and fixation of the patient's eyes on the object in real time video; and reviewing the real time video at a subsequent time to diagnose any eye disorders indicated by said Hirschberg and Brueckner reflexes.

Thus, the present invention overcomes the deficiencies of prior art eye medical devices which only provide static, non-real time images during an eye testing session. Further, the eye medical device of this invention uses existing camera mounting devices and implements inexpensive modifications to the camera to accomplish the objectives of this invention.

BRIEF DESCRIPTION OF THE DRAWINGS

In the accompanying drawings which form a part of the specification and are to be read in conjunction therewith and in which like reference numerals are used to indicate like parts in the various views:

FIG. 1 is a fragmentary side elevation view of a medical device constructed according to the present invention for detecting eye disorders and showing a beam of light directed from the device into the eye of a patient, parts of the device being shown schematically;

FIG. 2 is an enlarged, fragmentary front elevation view of the device taken generally along the plane of line 2—2 of FIG. 1 in the direction of the arrows and showing the light directing apparatus, phantom lines being used to illustrate rotational positioning of the light directing apparatus;

FIG. 3 is fragmentary, side elevation view of a forward portion of the device taken in vertical section along line 3—3 of FIG. 2 in the direction of the arrows;

FIG. 4 is an enlarged, fragmentary side elevation view of the light directing apparatus with portions being broken away for purposes of illustration;

FIG. 5 is an enlarged, top plan view of the light directing apparatus taken in horizontal section along line 5—5 of FIG. 2 in the direction of the arrows;

FIG. 6 is an enlarged, top plan view of the light directing apparatus taken generally along the plane of line 6—6 of FIG. 4 in the direction of the arrows;

FIG. 7 is an enlarged, top plan view of the medical device taken generally along the plane of line 7—7 of FIG. 1 in the direction of the arrows, and showing a mounting stand for video camera portion of the medical device;

FIG. 8 is a fragmentary, side elevation view of the mounting stand taken in vertical section along line 8—8 of FIG. 7 in the direction of the arrows; and FIG. 9 is a front, fragmentary perspective view of a patient illustrating the Brueckner and Hirschberg reflexes resulting from light focused on the patient's eyes.

DESCRIPTION OF THE PREFERRED EMBODIMENT

Turning now to the drawings in greater detail, and initially to FIGS. 1 and 2, a medical device useful in a method of the present invention is generally designated by the numeral 10. Medical device 10 is particularly adapted to focus a light source into a patient's eyes and record in real time video the images produced by the light reflected from the eyes along a line generally coincident with the light beam focused on the eyes. The video can then be analyzed by an eye specialist to diagnose certain defects and abnormalities of the patient's eyes.

The medical device 10 comprises a video image recorder such as a video camera 12 on which is mounted a light emitting apparatus 14 which is capable of focusing a beam of light 16 into one or both eyes 18 of a patient 20. The beam of light 16 can originate from a suitable source 22 or can be generated by the light emitting apparatus 14 itself. The beam of light 16 emitted from apparatus 14 can be a wide spectrum visible light or it can be of a narrow wavelength, including nonvisible wavelengths such as infrared light, as may be desired for particular diagnostic tests.

The light emitting apparatus 14 is mounted adjacent a lens 24 of the video camera 12 by a mounting bracket 26 which allows the beam of light 16 to be emitted from within the field of the lens aperture. Preferably, the mounting bracket 26 is adjustable to allow the position of the light beam 16 to be fixed at different positions within the field of the lens aperture and to also allow the light beam 16 to be moved outside of the field if desired.

Turning additionally to FIG. 3, the mounting bracket 26 is generally of a two piece construction and comprises a mounting collar 28 removably received within a flat plate 30. The lens mounting collar 28 is cylindrical in configuration and is received within a circular opening which is formed in the plate 30 concentrically with the hemispheric end. A forward portion of the collar 28 is sized slightly smaller than the diameter of the opening in the plate 30 to allow the collar to be inserted into the opening through the rear of the plate 30. An outwardly extending skirt 32 formed on the outer surface of collar 28 acts as a stop to prevent complete forward movement of the collar 28 through the plate 30. The collar 28 is then coupled with the plate 30 by a lock ring 34 which is slipped over the forward end of the collar 28 and seats within a suitable groove 36 in the outer surface of the collar. When seated in the groove 36, the lock ring 34 abuts a forward face 38 of a recessed portion of the plate 30. The plate 30 is thereby captured between the lock ring 34 and skirt 32 to prevent fore-and-aft movement between the collar 28 and plate 30 while still permitting rotational movement therebetween.

The collar 28 has an externally threaded rear portion which allows the collar 28 to be threaded onto internal threads of a housing 40 surrounding and extending outward from the video camera lens 24. It will be appreciated that other suitable means may be utilized for coupling the collar 28 with the lens housing 40 or other portions of the video camera 12. By using the removable collar 28, the mounting bracket 26 can be readily adapted for connecting with different types of video cameras by simply selecting the collar which is configured for the particular video camera being utilized.

The internal diameter of collar 28 should be selected to permit the desired surface area of the lens 24 to remain uncovered by the cylindrical wall of the collar 28. In some applications, it may be desirable to use a small internal diameter collar 28 to provide a small aperture for the lens 24. In other applications, it may be necessary for the collar 28 to have an internal diameter generally coinciding with the lens diameter, such as in those instances when it is desired that the light emitting apparatus 14 be offset from the center axis of the lens 24.

As is illustrated in FIG. 2, the plate portion 30 of the mounting bracket 26 can be rotated about the collar 28 to allow the light beam 16 emitted by the apparatus 14 to be placed in the desired quadrant of the lens. The plate 30 is held in the desired rotational position by the frictional engagement of the lock ring 34 and skirt 32 against the plate 30. However, if desired, a suitable mechanism (not shown) may be provided to positively lock the plate 30 in the desired position, including at preselected or incremental locations.

The light emitting apparatus 14 has a generally cylindrical body 42 which is mounted in a suitable fashion to an upper end of an elongated stem 44. A lower end of the stem 44 is slidably received within a holder 46 positioned at the lower end of a channel 48 cut into the mounting bracket plate 30. As can be seen in FIGS. 4–6, the stem 44 is free to move vertically along an internal slot 50 in the holder 46. Vertical movement of the stem 44 can be remotely controlled by a wire 52 which is connected to the lower end of the stem 44 and is routed through a hollow cable 54 to a location accessible by the operator of the video camera 12. The hollow cable 54 is itself held in place within the holder 46 by a suitable set screw 56.

Movement of the stem 44 longitudinally along the mounting bracket plate 30 allows the light emitting apparatus 14 to be correspondingly repositioned. This longitudinal movement of the light emitting apparatus 14, in combination with the rotational freedom of the mounting bracket plate 30, allows the light beam 16 to be directed from any desired position across the face of the video camera lens 24 as well as from positions outside of the lens aperture. This ability to move the beam of light 16 provides great flexibility in the types of diagnostic tests that can be performed using the medical device 10.

Returning to FIGS. 1 and 3, a fiber optic cable 58 is used to deliver the light beam 16 from the light source 22 to the light emitting apparatus 14. The fiber optic cable 58 is encased within a protective sheaf 60 and extends within the body of apparatus 14. A mirror 62 is placed at a 45 degree angle at the upper end of the light emitting apparatus 14 and reflects the light beam 16 from the fiber optic cable 58 toward the eyes 18 of patient 20. It will be appreciated that other suitable optics may be provided within the apparatus 14 for focusing the light beam 16 in the desired manner.

The video camera 12 which is used for recording the image generated by the light reflecting off of the patient's eyes is preferably a consumer grade S-VHS video camera, although other types of video image recorders can be used. The video camera 12 includes suitable controls 64 and a microphone 66 which can be used to record comments regarding the video images of the patient's eyes as well as identifying characteristics of the patient 20. A recording medium 68 such as a standard video tape is provided to record the visual images and audible comments in real time.

As shown in FIGS. 1 and 7, a stand 70 is provided for mounting the video camera 12 in a manner which allows for fore-and-aft movement of the video camera in the direction of the patient 20. The stand 70 comprises a tripod 72 which provides vertical positioning of the video camera 12 and is connected to a camera slide mount 74 which provides the fore-and-aft movement. Slide mount 74 includes a mounting plate 76 which is moveable along a pair of spaced apart, cylindrical rails 78 supported on a base 78. Frictional sleeves (not shown) can be provided on the rails 78 to retain the mounting plate 76 in the desired position along the rails 78. As can best be seen in FIG. 8, the video camera 12 is secured to the mounting plate 76 by a thumb screw 82 that extends vertically through the plate 76 and is threaded into the bottom of video camera 12. The video camera 12 rests on a circular platter 84 which is positioned on an upper surface of mounting plate 76 and allows the video camera to be rotated in a horizontal plane about the axis of the thumb screw 82. The stand 70 thus permits the video camera 12 to be readily adjusted to the precise position desired in relation to the patient's eyes 18 without requiring that the stand by lifted off of the floor. This ability to precisely position the video camera 22 permits the camera to be focused without adjusting the lens 24 and disturbing the selected spacing between the lens 24 and the light emitting apparatus 14.

In operation, the video camera 12 is directed at the eyes 18 of the patient 20 and is placed in the desired position by appropriate adjustment of stand 70. The light emitting apparatus 14 is then adjusted to direct the beam of light 16 upon one or both eyes 18 of the patient 20. The light beam 16 is then reflected from within the eyes 18 and a portion of the reflected light is directed back along a path generally coincident with the light beam 16. The image produced in the patient's eyes 18 can then be recorded on the recording medium 68 as a real time video segment.

In a method in accordance with the present invention for diagnosing eye disorders, the light beam 16 is directed from within the field of the video camera lens 24 and is focused into the eyes 18 of the patient 20 so that reflected light is received in the lens 24. The video image created in the patient's eyes is then recorded in real time video on the recording medium. The recorded segment should continue while the patient's eyes 18 focus on the lens 24 or other desired object. As the eyes 18 focus, constriction of the pupils can be observed, thus providing the necessary verification that any observed abnormalities in the pattern or placement of the reflected light is indicative of an underlying eye disorder rather than simply a result of the patient's eyes being unfocused. Typically, an individual can be quickly trained to operate the medical device 10 and obtain the necessary video of the patient focusing on the desired object. The video can then be edited and the appropriate segment forwarded to an eye specialist for review. This procedure allows the specialist to review as little as a few seconds of tape and determine whether there is an indication of a potential eye disorder. By viewing the tape which has been recorded in real time, the eye specialist can verify that the eyes of the patient are properly focused as evidenced by the constriction of the pupils which normally accompanies such fixation. This ability to observe the pupil constriction is crucial in being able to accurately diagnose certain tests such as the Hirschberg and Brueckner reflexes and cannot be achieved by observing still photographs.

It will be appreciated that the medical device 10 can be operated by non-eye specialists and the appropriate video segment needed for diagnostic purposes can be readily obtained, even from children and other typically noncompliant individuals. For example, the medical device 10 can be placed in a general practitioner's waiting room and operated by a nurse or receptionist. The video footage of a large number of patients can then be edited so that only the necessary footage from each patient is forwarded to an eye specialist for diagnosis. The diagnosis can then be provided to the patient without requiring that he or she actually visit the eye specialist.

It will be appreciated that the medical device 10 is particularly adapted for use in performing Hirschberg and Brueckner reflex tests. Referring to FIG. 9, for purposes of illustration, the eyes of a patient are shown reacting to Hirschberg and Brueckner reflex tests. The patient's left eye 18a demonstrates a positive Brueckner reflex as indicated by the bright diffuse reflex 100. In contrast, the patient's right eye 18b demonstrates a negative Brueckner reflex as indicated by the lack of a corresponding bright diffuse reflex. The Hirschberg reflex is indicated by the beam of light reflecting off the surface of the eyes 18a and 18b to form small fixing points 102 and 104, respectively. Eye asymmetry is demonstrated by displaced fixing point 102 because the beam of light does not reflect off the same portion of eye 18a as on the Hirschberg reflex fixing eye 18b where the fixing point 104 is centrally positioned. Thus, trained technicians can take a sufficiently long real time video segment of the beam of light incident upon the eyes of a patient to ensure that sufficient data is obtained for proper diagnosis by the eye specialist. The ability for nonskilled personnel to acquire proper data is, therefore, substantially increased over prior art methods which utilize static photography means.

The medical device 10 is also adapted for performing other eye diagnostic tests, such as determining refractive errors and astigmatism. The ability to move the light emitting apparatus 14 while the patient remains focused on a specific object is particularly notable because it allows the light beam 16 to be directed onto patient's eyes 18 from different angles. The dynamic reflected images which are produced allow the eye specialist to obtain a more complete examination of the total surface and internal portions of the eye, thereby enhancing the specialist's ability to detect and diagnose eye disorders.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limiting sense.

Having thus described the invention, what is claimed is:

1. A medical device for recording images of a light beam reflected off of the eyes of a patient, the device comprising:

a video image recorder for recording real time video of the eyes of the patient and including a lens for focusing a video image onto a recording medium;

a light emitting device coupled with the video image recorder for directing a beam of light into the eyes of the patient; and means for movably mounting the light device on the video image recorder to allow the beam of light to be directed from variable positions within a field of the lens so that light reflected from the patient's eyes and recorded onto the recording medium travels along a path generally coincident with that of the beam of light.

2. The medical device of claim 1, including a stand having means for movably mounting the video image recorder to adjust the distance from the video image to the eyes of the patient.

3. The medical device of claim 2, wherein the means for mounting the light emitting device comprises a mounting bracket having a first portion connect to the video image recorder and a second portion rotatably coupled with the first portion and mounting the light emitting device.

4. The medical device of claim 3, including means carried on said second portion of the mounting bracket for moving said light emitting device along said second portion.

5. A medical device for performing Hirschberg and Brueckner reflex tests on the eyes of a patient without the immediate assistance of an eye specialist, the device comprising:

a video camera having a lens for receiving video images and being adapted to removably receive a storage medium for recording real time video images of the eyes of the patient;

means for movably mounting the video camera to direct and focus the lens on the eyes of the patient;

a lighting device for producing a beam of light; and means for movably mounting the lighting device on the video camera to direct the beam of light into the eyes of the patient from within a field of the video camera lens.

6. The medical device of claim 5, wherein the movable light mounting means comprises means for adjusting the position of the lighting device in vertical and arcuate directions.

7. The medical device of claim 6, wherein the adjusting means comprises a collar connected to the video camera and a plate member rotatably on the collar to provide for arcuate movement of the plate about the lens of the video camera.

8. The medical device of claim 7, wherein the adjusting means further comprises a holder affixed to the plate and a movable stem supported in the holder and connected to the lighting device to permit said vertical movement.

9. A method for performing Hirschberg and Brueckner reflex tests on the eyes of an individual without the immediate assistance of an eye specialist, the method comprising the steps of:

directing a beam of light from within a field of a lens of a video camera onto the eye of the individual to produce Hirschberg and Brueckner reflexes;

focusing the eyes of the patient on an object while the Hirschberg and Brueckner reflexes are produced;

recording the Hirschberg and Brueckner reflexes and fixation of the patient's eyes on the object in real time video; and reviewing the real time video at a subsequent time to diagnose any eye disorders indicated by said Hirschberg and Brueckner reflexes.

10. The method as set forth in claim 9, including the step of moving the beam of light while the patent's eyes are focused on the object and recording the Hirschberg and Brueckner reflexes while the beam of light is moving.

11. The method as set forth in claim 9, including the step of editing the real time video to produce a segment of approximately 5 seconds in length which contains the recorded Hirschberg and Brueckner reflexes and the fixation of the patient's eyes on the object and then forwarding the segment to an eye specialist for said diagnosis.

12. The method as set forth in claim 9, wherein said step of directing a beam of light comprises the step of directing a beam of infrared light.

* * * * *